(12) United States Patent
Gerhardt et al.

(10) Patent No.: US 6,413,398 B1
(45) Date of Patent: Jul. 2, 2002

(54) METHOD FOR ELECTROCHEMICAL DETECTION

(75) Inventors: Geoff Charles Gerhardt, Folsom, CA (US); Richard Murray Cassidy; Andrzej S. Baranski, both of Saskatchewan (CA)

(73) Assignee: Her Majesty the Queen in right of Canada, as represented by the Canadian Food Inspection Agency, Saskatoon (CA)

( * ) Notice: Subject to any disclaimer, the term of this patent is extended or adjusted under 35 U.S.C. 154(b) by 0 days.

(21) Appl. No.: 09/394,654

(22) Filed: Sep. 13, 1999

(51) Int. Cl.$^7$ ................................................ G01N 27/26
(52) U.S. Cl. ...................... 204/452; 204/603; 204/402; 205/775; 205/794.5
(58) Field of Search ................................. 204/450, 451, 204/452, 402, 603; 205/775, 794.5

(56) References Cited

U.S. PATENT DOCUMENTS

| | | | |
|---|---|---|---|
| 4,496,454 A | * 1/1985 | Berger | 204/402 |
| 4,601,792 A | * 7/1986 | Tenygl | 205/794.5 |
| 5,611,909 A | * 3/1997 | Studer | 205/775 |

FOREIGN PATENT DOCUMENTS

GB      2059073 A   * 9/1981

OTHER PUBLICATIONS

CAPLUS abstract of Seryakov (RU 2114434 C1).*

Caudill et al., "Liquid Chromatography with Rapid Scanning Electrochemical Detection at Carbon Electrodes," *Anal. Chem.*, vol. 55, (1983) pp. 1877–1881.

Curry Jr., et al., "Electrochemical Detection for Capillary Electrophoresis," *Electroanalysis*, vol. 3 (1991) pp. 587–596.

Ferris et al., "Scanning Electrochemical Detection in Capillary Electrophoresis," *Microcol. Sep.*, vol. 6 (1994) pp. 263–268.

Gerhardt et al., "Square–Wave voltammetry Detection for Capillary Electrophoresis," *Anal. Chem.*, vol. 70 (1998), pp. 2167–2173.

Goto et al., "Rapid–Scanning Electrochemical Detector with Micro Working Electrode for Micro High–Performance Liquid Chromatography," *Chromatographia*, vol. 21 (1986) pp. 631–634.

Haber et al., "Potentiometric Detector for Capillary Zone Electrophoresis," *Chimia*, vol. 45 (1991) pp. 117–121.

Huang et al., "Quantitative Analysis of Low Molecular Weight Carboxylic Acids by Capillary Zone Electrophoresis/Conductivity Detection," *Anal. Chem.* vol. 61 (1989) pp. 766–770.

Kappes et al., "Potentiometric detection of inorganic anions and cations in capillary electrophoresis with coated–wire ion–selective electrodes," *Analytica Chimica Acta*, vol. 350 (1997) pp. 141–147.

(List continued on next page.)

*Primary Examiner*—T. Tung
*Assistant Examiner*—Abi Noguerola
(74) *Attorney, Agent, or Firm*—Knobbe, Martens, Olson & Bear LLP (57) ABSTRACT

A method for electrochemical detection (ECD) is disclosed. The illustrated embodiments are particularly adapted to use in detection of analytes separated by capillary electrophoresis. The method is a voltammetric ECD, including a preparatory positive potential pulse, an optional stabilizing pulse at a negative potential, an analytical pulse at extreme negative potentials (e.g., –300 mV to –1,500 mV), and a positive cleaning potential pulse. The methods have been shown to detect analytes previously considered to be electrochemically inactive using more traditional electrochemical methods. Examples of such analytes include various drugs, antibiotics, and peptides.

32 Claims, 7 Drawing Sheets

OTHER PUBLICATIONS

Matysik, F.M., "Improved end–column amperometric detection for capillary electrophoresis," *Journal of Chromatography A*, vol. 742 (1996) pp. 229–234.

Mikkers et al., "High–Performance Zone Electrophoresis," *J. of Chromatog.*, vol. 169 (1979) pp. 11–20.

Osteryoung et al., "Square Wave Voltammetry," *Anal. Chem.*, vol. 57 (1985) pp. 101A–110A.

Park et al., "Voltammetric Detection for Capillary electrophoresis," *Anal. Chem.*, vol. 69 (1997) pp. 2994–3001.

Voegel et al., "Electrochemical detection in capillary electrophoresis," *Electrophoresis*, vol. 18 (1997) pp. 2267–2278.

Wallingford et al., "Capillary Zone Electrophoresis with Electrochemical Detection," *Anal. Chem.*, vol. 59 (1987) pp. 1762–1766.

White et al., "Scanning On–Column Voltammetric Detector for Open–Tubular Liquid Chromatography," *Anal. Chem.*, vol. 58 (1986) pp. 293–298.

Yik et al., "Capillary electrophoresis with electrochemical detection," *Trends Anal. Chem.*, vol. 11 (1992) pp. 325–332.

\* cited by examiner-

METHOD FOR ELECTROCHEMICAL DETECTION

FIELD OF THE INVENTION

The present invention relates generally to the field of chemical analysis. More specifically, the invention relates to a method for electrochemical detection at low potentials.

BACKGROUND OF THE INVENTION

Chemical analysis is widely used in modem society to examine samples obtained from a variety of sources to determine the presence or absence of analytes of interest. Examples include: drug detection in human and animal tissue and secretions; detection of contamination in water, food and the environment; scientific research; and medical diagnosis. In the food industry, for example, chemical analysis is routinely used to analyze a large number of tissue samples from food-producing animals. In this way, drug residue levels can be determined for food safety purposes. Regardless of the application, techniques for chemical analysis should be rapid, performable by laboratory technicians, inexpensive, and sensitive.

Currently, high performance liquid chromatography (HPLC) is the most common method of separating analytes for analysis. Although HPLC provides good selectivity for this application, it has several drawbacks. The most significant of these is its high cost of operation. HPLC uses high-cost equipment and consumables. In addition to these costs is the increasing cost of disposing of the hazardous solvent waste generated by HPLC. Capillary electrophoresis (CE), first reported in the early nineteen eighties, has developed into a technique with a substantial application base and commercial support. Because CE does not suffer from the same high cost of operation as HPLC, it would seem to be a good replacement.

Analytical methods such as Flow Injection Analysis (FIA) use selective chemical transformation of an analyte, rather than separation, to enable one analyte to be detected or quantified in the presence of another. The chemical modification is carefully selected to allow the desired substance (s) to register on a suitable detector, while components of the mixture that are not modified do not register.

Once the constituents of a fluid are separated by CE or another suitable separation scheme, or are chemically modified by FIA or similar method, they must be analyzed by a detection system that identifies and preferably also quantifies the level of each separated or modified constituent. Commercially available detection methods for use in conjunction with CE separation do not provide particularly high sensitivity.

UV detection has been the most popular detection system available for use in conjunction with CE separation. UV detection is a mass-dependent detection method, however, and its sensitivity is severely compromised by the short light path lengths encountered in CE. Laser-induced fluorescence has been used to achieve sensitive detection but is limited to compounds which fluoresce or are amenable to being tagged with a fluorophore.

Another method of detection is amperometric electrochemical detection. See, e.g., Wallingford et al., 1987 Anal. Chem. 59: 1762–1766. Wallingford et al. describe an amperometric electrochemical detection (ECD) for CE with a carbon fiber electrode inserted into a detection capillary. The detection capillary, in turn, is butted up to the CE separation capillary. The separation and detection capillaries are joined using an ion-conductive material through which the separation current could flow. Using this configuration, the ECD system is effectively decoupled from the CE separation field. When using a carbon fiber electrode inserted into the end of the capillary, a decoupling system is employed to avoid a high voltage drop along the length of the fiber electrode within the capillary, parallel to the separation field. A large number of amperometric-based CE-ECD reports followed with improved decoupling systems.

Despite these improvements, such field-decoupling systems are difficult to construct, fragile and impractical for many applications. Disk electrode systems, which do not require field decoupling systems, employ a disk electrode at the end of the separation capillary, normal to the separation field. Although the potential of the sensing electrode is shifted by the separation field, this potential shift is constant across the electrode surface and can therefore be accounted for by including an "offset" in the potential applied to the sensing electrode. Unfortunately, disk-electrode systems typically demonstrate sensitivities significantly lower than those of the more complex carbon-fiber electrode, field-decoupled CE-ECD systems.

Amperometric ECD detection has proven a fairly sensitive ECD mode used for CE. Other ECD modes, such as conductionmetric and potentiometric detection, are typically less sensitive and apply only to a narrow group of analytes. Voltammetric ECD is also generally less sensitive than amperometric detection. In conjunction with HPLC and CE separation systems, however, lower sensitivities are traded off against additional qualitative information in the form of potential-based current response.

The sensitivity of voltammetry-based ECD is somewhat improved though square-wave voltammetry (SWV). Hardware particularly adapted employing SWV in electrochemical detection of analytes in a CE separated stream is described in Gerhardt et al., "Square-Wave Voltammetry for Capillary Electrophoresis," 1998 Anal. Chem. 70, pp. 2167–2173.

However, even with the newly developed CE-SWV system, detection of some analytes was still not possible.

SUMMARY OF THE INVENTION

In accordance with one aspect of the invention, a method is provided for electrochemical detection of an analyte in a fluid. The method includes providing a working electrode with a diameter of about 1 $\mu$m to 100 $\mu$m in association with the fluid. A first positive potential pulse is applied to the fluid at the working electrode at a voltage of less than about 1,000 mV. A negative analytical potential pulse is applied to the fluid at the working electrode at a voltage between about 0 mV and –2,000 mV. The current flow through the working electrode is measured during the analytical potential pulse.

In accordance with another aspect of the present invention, an electrochemical detector is provided. The detector includes electronic hardware and software controlling voltage applied to a sample fluid. Voltage is applied in repeated cycles of pulses, where each cycle includes: a positive electrode preparation pulse of a first magnitude; a negative analytical pulse; and a positive cleaning pulse of a second magnitude greater than the first magnitude.

The methods and apparatus described herein permit electrochemical detection of analytes previously thought to be electrochemically inactive. Using these methods and apparatus, analytes produce a positive current flow and a good detection sensitivity.

These and other aspects of the invention will be readily apparent to the skilled artisan in view of the disclosure herein and the appended claims.

DETAILED DESCRIPTION OF THE PREFERRED EMBODIMENTS

The present invention provides particularly sensitive methods for electrochemical detection. These methods have been found to register analytes previously thought to be electrochemically inactive (for the purpose of analytical detection). Although described in conjunction with a particular chemical separation apparatus, the skilled artisan will readily find application for the principles described herein for electrochemical detection of analytes in a number of other contexts. While applicable to detection in standing solutions, the preferred embodiments have particular utility in conjunction with flowing systems, such as capillary electrophoresis (CE), liquid chromatography (all types including HPLC), capillary electrochromatography, and flow injection analysis, among others.

Preferred Apparatus

Figure 1:
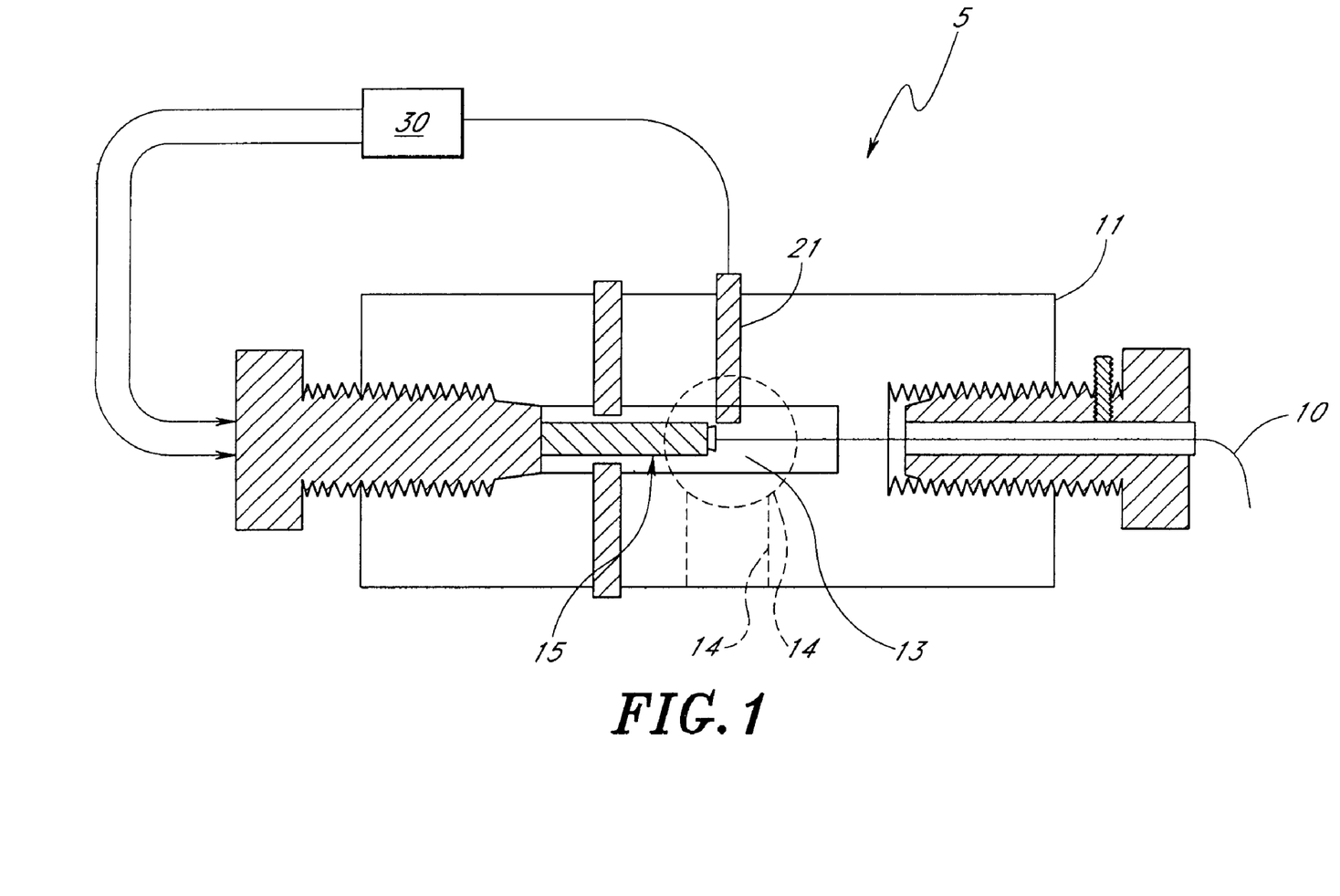
FIG. 1 is a schematic cross-section of an apparatus for electrochemical detection of analytes separated by capillary electrophoresis, constructed in accordance with preferred embodiments of the present invention.
Figure 2:
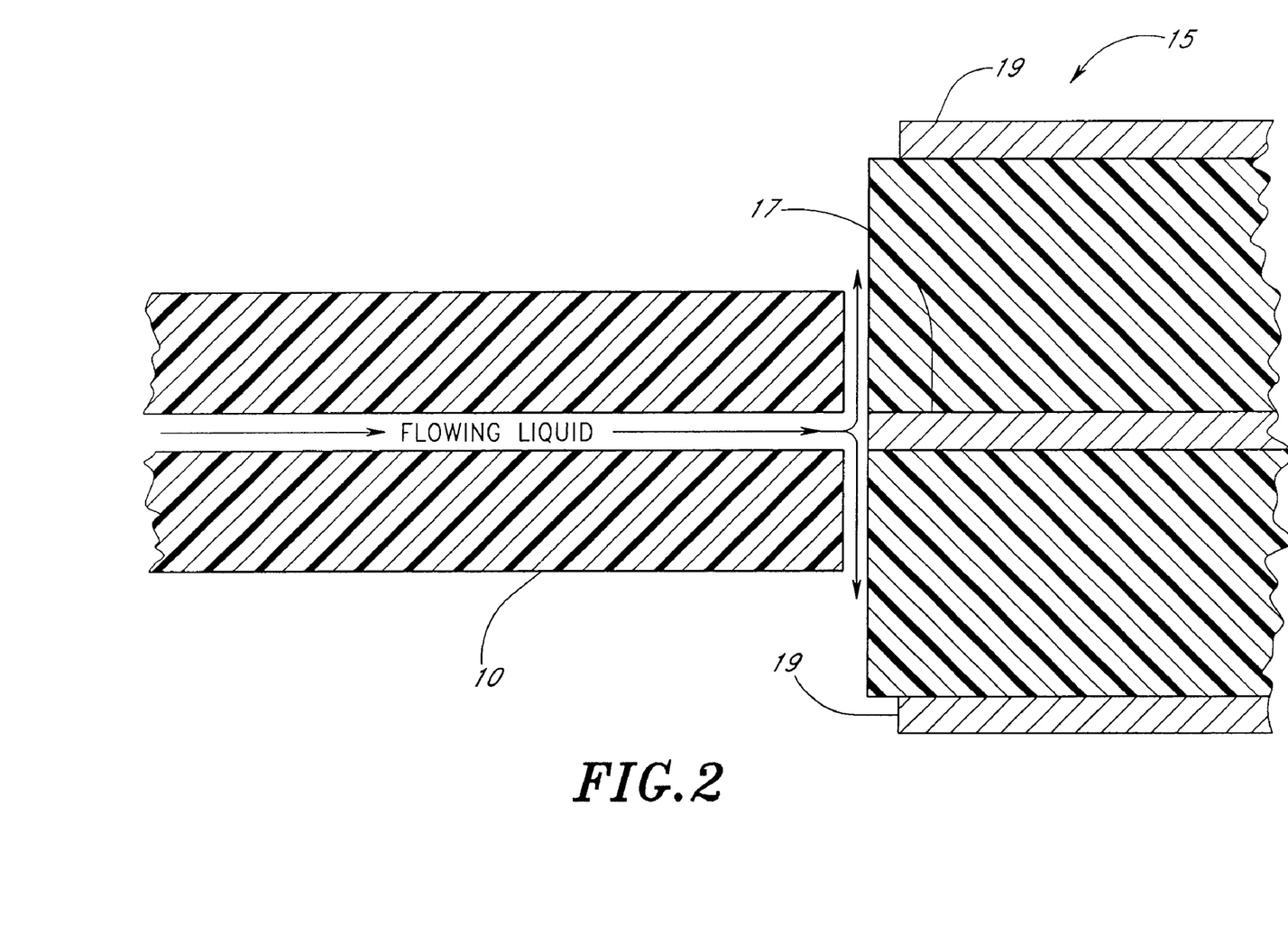
FIG. 2 is an enlarged view of an electrode assembly for the apparatus of FIG. 1.

FIGS. 1 and 2 schematically illustrate an electrochemical detection (ECD) system or detector 5, constructed in accordance with the preferred embodiment of the present invention. With the exception of electronic controls for the electrodes of the electrochemical detector 5, the illustrated hardware is adapted from the disclosure of Gerhardt et al., "Square-Wave Voltammetry for Capillary Electrophoresis," 1998 Anal. Chem. 70, pp. 2167–2173, the disclosure of which is incorporated by reference herein.

The outlet end of a liquid conduit 10 is extended through a cell housing 11 and empties into a reservoir 13 filled with an electrolyte. An inlet and an outlet 14 are provided for filling and emptying the reservoir of electrolyte between analyses. The electrolyte preferably has a concentration of greater than about 1 millimole/L (millimolar), and in the illustrated examples set forth below, buffer solutions have a concentration of about 100 millimolar.

In the illustrated embodiment, the conduit 10 carries analytes separated by capillary electrophoresis. The illustrated reservoir 13 has a volume of about 0.5 mL. An electrode assembly 15 protrudes into the reservoir 13 in proximity to the conduit 10 outlet. As best seen from FIG. 2, the electrode assembly 15 includes a working electrode 17 of small surface area, and a coaxial auxiliary electrode 19 of much larger surface area than the working electrode 17.

Referring still to FIG. 2, the working electrode 17 is positioned proximate the exit opening of the conduit 10. The conduit 10 carries analytes, preferably separated by an upstream separation system (not shown), in a flowing fluid. In the illustrated embodiment, the separation system comprises a capillary electrophoresis (CE) system, and separates analytes in an identifiable sequence within the flow. Accordingly, particular analytes can be identified by the time they are detected by the illustrated detection system 5.

The working electrode 17 is configured for low potential operation. In particular, the electrode 17 preferably has a diameter or width of less than about 100 $\mu$m, and more preferably less than about 50 $\mu$m. The illustrated working electrode 17 has a diameter of about 25 $\mu$m. Advantageously, the small surface area of the electrode 17 facing the conduit 10 facilitates rapid diffusion of reactants and reaction products to and from the electrode during relatively high potential cleaning pulses and extreme low potential detection, as described below in connection with the method of operation. Such rapid diffusion facilitates extreme potential excursions in both the cleaning and detection stages of the waveform. The rapid diffusion of gases produced during these extreme potentials diffuses from the electrode surface before coalescing into bubbles, which would otherwise hinder electrochemical measurements in these potential regions.

The working electrode 17 preferably comprises a metal exhibiting good corrosive resistance and strong electrocatalytic properties. Exemplary metals include platinum (Pt), palladium (Pd), gold (Au), ruthenium (Ru), rhodium (Rh), osmium (Os) and iridium (Ir). The detection system 5 has been demonstrated with a platinum electrode 17 and with a palladium electrode 17. Oxides of both platinum and palladium exhibit catalytic or adsorptive characteristics.

A reference electrode 21 also is inserted into the reservoir 13, serving to measure the potential of the solution while the auxiliary electrode 19 controls the solution potential in the reservoir 13. The voltages described hereinbelow are relative to a silver-silver chloride (Ag|AgCl) reference electrode 21. The skilled artisan can readily convert the voltages herein for systems using other reference electrodes.

The detection system 5 further comprises an electrical controller 30, represented schematically in FIG. 1. The controller 30 represents software and electronics configured to operate the electrode assembly 15 in conjunction with feedback from the reference electrode 21. The electrodes 17, 19, 21 with the associated electrical controller 30 are configured for voltammetric ECD, and particularly for high-frequency square-wave voltammetry in the illustrated embodiment.

As will be appreciated by the skilled artisan, the controller 30 comprises a microcontroller; a potentiostat directed by the microcontroller and capable of applying rapid potential steps; a fast current amplifier; and software for directing the desired voltage waveforms and for collecting and presenting the collected data. The potentiostat controls the potential of the auxiliary electrode 19 relative to the reference electrode 21. The amplifier both converts the current produced at the working electrode 17 to a voltage and amplifies it to a level suitable for digitization or other signal processing operations. The microcontroller synchronously collects current data while applying potential changes to the auxiliary electrode19 and stores or plots the data as a function of time and the corresponding voltage at the auxiliary electrode 19. This data is analyzed by standard techniques used in square-wave voltammetry to determine the fraction of the electrical current attributable to the presence of the analyte at the working electrode 17.

Method of Operation

Figure 9:
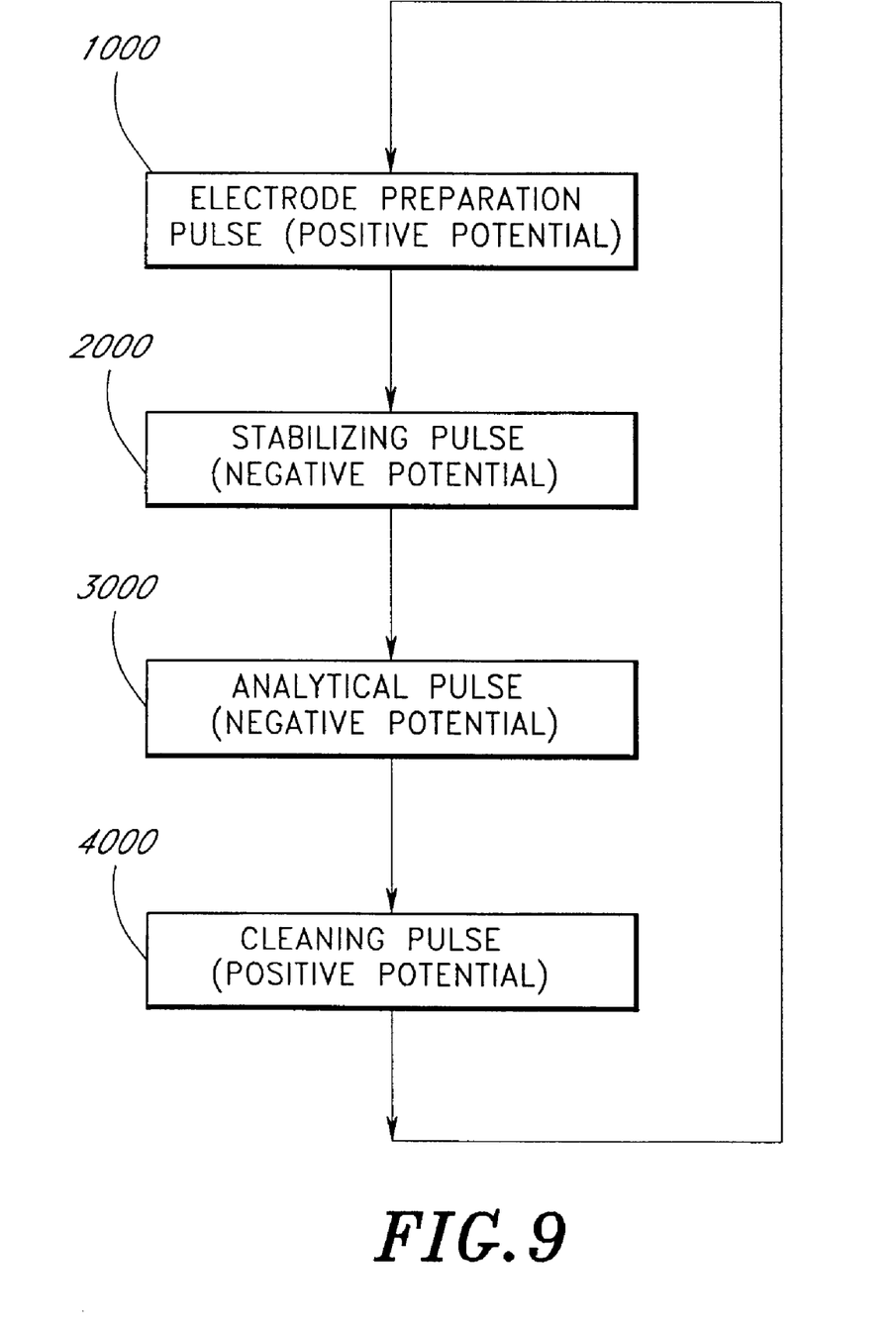
FIG. 9 is a flowchart showing phases in a cycle of electrochemical detection in accordance with the preferred methods.

Methods of detecting analytes with the above-described apparatus will now be described with reference to FIGS. 3 and 9. The skilled artisan will readily appreciate, however, that the methods described herein will also have application to other apparatus. As noted, voltages are given for an Ag|AgCl reference electrode.

Figure 3:
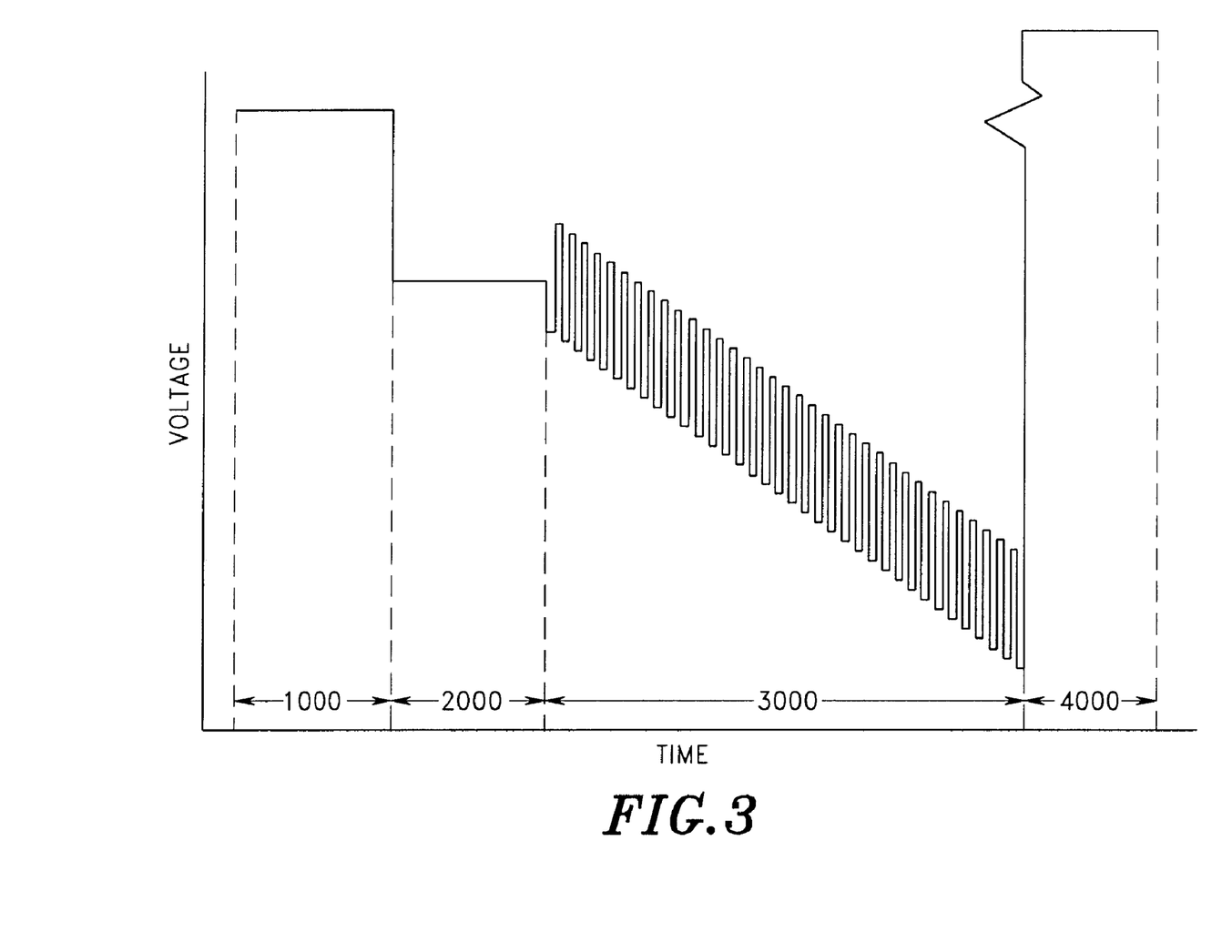
FIG. 3 is a voltage-time chart for an electrochemical detection cycle, in accordance with the preferred embodiments.

With reference to FIG. 3, the potential profile applied to the working electrode, which is effectively of the same magnitude but opposite in sign to that applied to the auxiliary electrode, is shown for a single measurement cycle. Reference is also made to the flow chart of FIG. 9, illustrating the cyclic nature of the applied voltages. In the illustrated embodiment, the potential profile includes four distinct phases: a first pre-analytical pulse 1000; a second pre-analytical pulse 2000, an analytical pulse 3000; and a post-analytical pulse 4000. Since the profile is but one cycle in a continuous series of such pulses, it will be understood that the post-analytical pulse 4000 can be considered a pre-analytical pulse for the subsequent measurement cycle.

Briefly, the first pre-analytical pulse 1000, serves to prepare the electrode for the analytical portion of the cycle, in accordance with the preferred embodiment. The second pre-analytical pulse serves to stabilize the system prior to analysis. The analytical pulse is the portion of the cycle during which current readings are recorded to determine the presence and/or concentration of analytes in the solution in contact with the electrode. Finally, the post-analytical pulse serves to clean the electrode of analytes and any other adsorbed contaminants for the next cycle.

Each of the four illustrated pulses are preferably conducted for between about 1 millisecond (ms) and 100 ms, more preferably between about 5 ms and 20 ms, and most preferably for about 5 ms to 10 ms. The analytical cycles are thus applied at a frequency of about 2.5 Hz to 250 Hz, preferably at greater than about 5 Hz, more preferably about 25 Hz to 50 Hz. The duration of the preferred pulses is selected for high-speed detection method of closely spaced analytes separated by capillary electrophoresis (CE). Peak widths in CE are commonly less than about 2 seconds, calling for detection frequencies of at least about 5 to 10 Hz. Greater frequency, of course, enables better resolution of peaks. For other separation techniques, these ranges can differ. For example, analytes separated by high pressure liquid chromatography (HPLC) can be analyzed with a reduced frequency, as compared to CE.

The individual potential pulses 1000–4000 and their functions will now be described in more detail.

The first pre-analysis or preparatory pulse 1000 prepares the electrode for analysis. A positive voltage is applied, desirably at a lower voltage than the cleaning pulse 4000 of the preceding cycle. Preferably, the preparatory pulse 1000 is conducted at a magnitude of less than about 1,000 mV and more preferably less than about 800 mV, and most preferably between about 300 mV and to 600 mV. For the illustrated arrangement, the preparatory pulse 1000 is conducted at flat, positive potential of about 400 mV.

The reduced potential, positive pulse during this phase 1000 has been found to increase sensitivity of the detection, relative to conducting only a post-analytical pulse. The preparatory pulse 1000 converts a surface termination formed during the preceding cleaning pulse 4000 to a more catalytically or adsorptively active surface. For example, in the illustrated embodiments, a platinum working electrode 17 (FIG. 2) is converted to $PtO_2$ during the cleaning pulse 4000. The preparatory pulse 1000, at a lower potential, converts this surface to a more catalytically active form of oxide (PtO).

Following the preparatory pulse 1000, the voltage is dropped to a negative potential in the range desired for the analytical pulse 3000.

Optionally, the potential can be stabilized during a second pre-analytical or stabilizing pulse 2000, prior to conducting the analytical phase. Preferably, the stabilizing pulse 2000 is a flat negative potential equal to the starting voltage of the analytical pulse 3000, described in more detail below. Thus, the stabilizing pulse is preferably conducted at between about −200 mV and −2,000 mV, more preferably between about −600 mV and −1,200 mV, and is at about −600 mV in the illustrated embodiment.

While not critical to attaining the advantages of the preferred embodiments, it has been found that employing the stabilizing pulse 2000 avoids false readings and can improve accuracy of the detection method by up to 20–30%.

The analytical pulse 3000 allows for detection at negative potential, preferably between about −200 mV and −2,000 mV, more preferably between about −300 mV and −1,500 mV, and most preferably between about −600 mV and −1,100 mV. Preferably, the pulse 3000 comprises a scan across a range of negative potentials within these ranges. The illustrated embodiment comprises a linear ramp conducted from about −600 mV down to −1,100 mV, and additionally includes a superimposed square-wave form with an amplitude of about 100 mV and a frequency of about 1000 Hz. While the potential ranges employed by the preferred embodiments differ from those disclosed in Gerhardt et al., incorporated by reference above, the waveform of the illustrated analytical pulse 3000 and interpretation of the subsequent current response is taken from square-wave voltammetry (SWV), discussed and referenced further in Gerhardt et al.

In other arrangements, a fixed negative potential within the preferred potential ranges can be employed during the analytical pulse 3000. For example, in one embodiment, the potential is fixed at about −900 mV during this phase. Current measured during a fixed-potential analytical pulse will be proportional in value to the concentration of the analyte dissolved in the solution in contact with the sensing electrode.

The post-analytical or cleaning pulse 4000 is a positive potential pulse at a relatively high magnitude. Preferably, the cleaning pulse 4000 is conducted at between about 700 mV and 3,000 mV, more preferably between about 800 mV and 2,000 mV, and most preferably between about 900 mV and 1,200 mV. In the illustrated embodiment, the cleaning pulse is a flat positive pulse at about 1,000 mV.

As is known in the art of voltammetry, the positive potential cleaning pulse 4000 oxidizes the working electrode 17 (FIG. 2). In the case of platinum electrode, for example, $PtO_2$ readily forms on the electrode during the relatively high magnitude, positive pulse 4000. In the process of oxidizing the surface, analytes and any other solutes attracted to the working electrode 17 during the negative analytical pulse 3000, are cleaned from the electrode for the next cycle. The small electrode 17 of the illustrated embodiment enables rapid diffusion of the repelled particles away from the working electrode 17, facilitating the high frequency detection called for by CE separation.

Results

The results of the above-described detection process are gathered and analyzed by generally known voltammetric methods. The presence of an analyte in solution at the working electrode is observed as a change in the current/time profile during the analytical pulse 3000 portions of the detection cycles. The electrical controller 30, including software and hardware for gathering, recording and displaying current data during the analytical pulses 3000, produce electropherograms such as FIGS. 5, 7 and 8, discussed in more detail below. Peaks in the electropherograms are correlated to their analytes by the time of their detection, as dictated by the operating parameters of the separation apparatus (not shown).

The inventors have found that detection by the above-described processes enables extremely sensitive detection of a much wider range of analytes than traditional electrochemical detection methods allow. For an analyte to be detectable using ECD in concentrations of analytical importance (i.e., less than about $10^{-5}$ moles/liter), the analyte must react electrochemically at an electrode within a potential range dictated by the electrode-electrolyte system. Because most separation processes (HPLC, CE, FIA) use aqueous-based separation media, it is usually the electroactivity of water at the chosen electrode that defines the "analytically useful" potential range. Within a limited potential region, only small currents are observed due electrochemical activity of the electrode-electrolyte system. These small currents are typically due to changes in the electrode-electrolyte double layer. In this potential region, the small currents produced by electrochemical reaction of analytes can be measured. When potentials outside this "inactive" region are used, though, the high currents produced by the electrochemical activity of the electrode-electroyte system (i.e. oxidation of the electrode, reduction of hydrogen ions to diatomic hydrogen) make measurements of the comparatively small analyte responses extremely difficult. It is this phenomena that conventionally limits the applicability of ECD to only those analytes which will react electrochemically in this narrow potential region. Although this analytically useful potential region can be shifted by carefully selecting appropriate electrode materials and electrolytes which are inactive in the region of interest, practicing electroanalytical chemists have found that the limited potential regions offered by most electrode-electrolyte systems restricts the applicability of ECD to a rather small fraction of the analytes typically separated by CE, HPLC or FIA. Because of this limited applicability, ECD has not been a popular detection method for these separation systems.

Using the preferred embodiments, analytes conventionally considered "electrochemically inactive" are detectable even in extremely low in the concentrations. For such analytes, conventional electrochemical techniques are sensitive to concentrations greater than about $10^{-5}$ molar, whereas the preferred method is preferably sensitive to concentrations less than about $10^{-5}$ molar, more preferably less than about $10^{-7}$ molar, and most preferably less than or equal to $10^{-8}$ molar.

Analytes which respond poorly to traditional ECD but which are in fact detectable by the disclosed methods of ECD, include many chemicals of analytical importance, including drugs, hormones, polypeptides, and other organic species. In particular, the disclosed detection methods have been found to be sensitive to analytes that have any appreciable amount of π-electron density, regardless of their susceptibility to oxidation/reduction, and further that the sensitivity of the present techniques is related to the amount of π-electron density. The greater the π-electron density, the greater the tendency of the species to chemisorb onto catalytically active surfaces. Organic compounds with π-electron-rich phenyl ring systems, carboxylic acids, ketones or other unsaturated functionality respond particularly well to the disclosed detection methods. Excellent responses have also been observed for analytes containing sulfur in its −2 oxidation state (e.g., the amino acid methionine). This response is likely due to the available electron density in the non-bonding valence electrons present in sulfur (−2).

Figure 4:
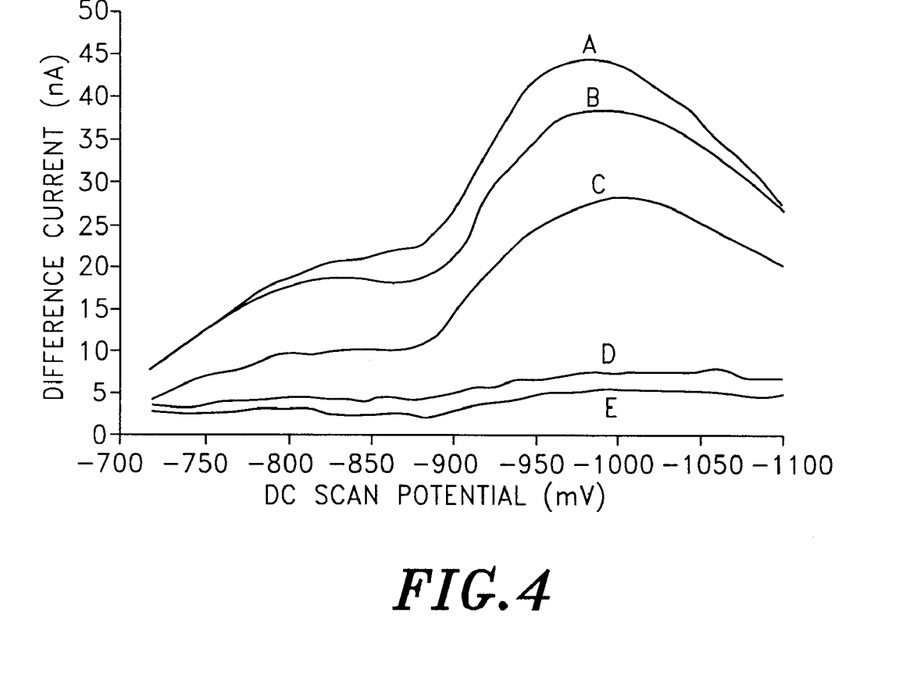
FIG. 4 is a voltammogram of several amino acids.
Figure 5:
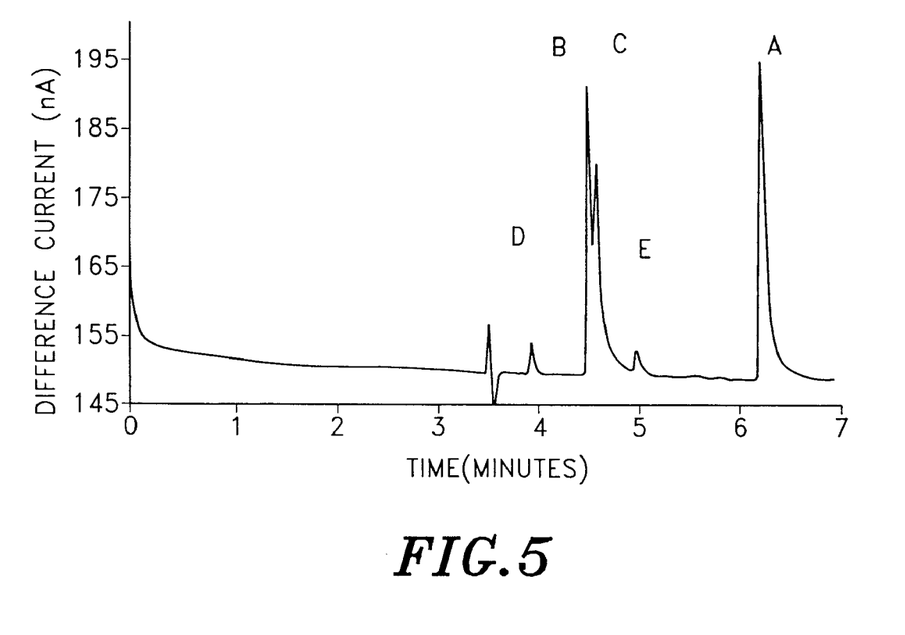
FIG. 5 is a capillary electrophoresis electropherogram of the amino acids, in accordance with the preferred embodiments.
Figure 6:
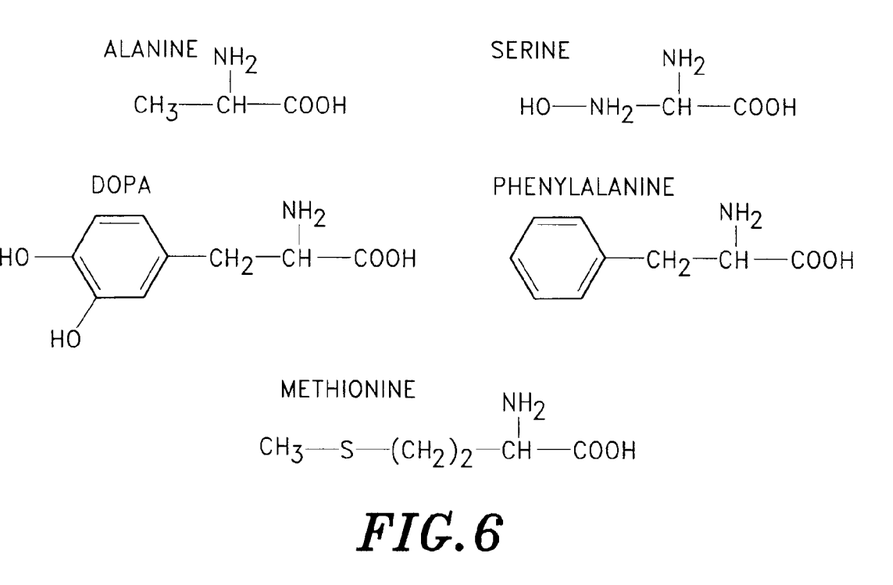
FIG. 6 illustrates the chemical structures of amino acids analyzed by the charts of FIGS. 4 and 5.

FIGS. 4 to 6 illustrate a correlation between π-electron density and sensitivity of the present ECD techniques.

With reference initially to FIG. 5, the chemical structures of five amino acids are shown. The benzene structures of DOPA and phenylalanine lend a relatively high π-electron density to these amino acids. Alanine and serine, while possessing some π-electron density due to their carboxyl groups, have relatively low π-electron densities. Methionine, though similarly low in π-electron density, responds well to the above-described detection methods due to the sulfur atom's nonbonding electrons.

FIG. 4 is voltammogram showing background-subtracted current against a DC potential of an SWV analytical pulse. The analysis was conducted on a sample containing the five amino acids of FIG. 6. Scans were captured during a capillary electrophoresis (CE) separation as each analyte zone exited the capillary, and the data from the various analytes were compiled into a single graph. During the SWV analytical pulse, the DC potential scanned from −700 mV to −1,100 mV in 100 ms. A square-wave form with a frequency of 1,000 Hz and an amplitude of 100 mV was superimposed upon this DC ramped potential scan.

In FIG. 4, the flat response of alanine and serine across the voltage scan, as compared to the steep response of current to voltage changes for each of the other three amino acids, indicates that the methods described herein are sensitive to the π-electron density of the analyte.

FIG. 5 is an electropherogram, showing the current spikes created by the introduction of each analyte sequentially after CE with a separation voltage of 10 kV. By the characteristic separation times produced by the CE, the peaks can be identified with particular analytes. While alanine and serine are small peaks, they are easily identified above the noise level.

The inventors have found that the preparatory potential pulse 1000 (FIG. 3), after a cleaning pulse 4000 and before analysis 3000, considerably enhances sensitivity of the present ECD techniques. With a platinum electrode, the high potential cleaning pulse produces a platinum dioxide ($PtO_2$) surface on the working electrode. The preparatory pulse 1000, at a lower but still positive voltage, converts the $PtO_2$ surface to the more catalytically active PtO. Accordingly, adsorption of organic analytes onto the working electrode surface is enhanced.

The adsorption of the analytes onto the catalytically activated electrode surface produces a significant current response during the extreme negative potential detection pulse, presumably due to the decomposition of these analytes. In contrast, conventional ECD techniques monitoring currents using more moderate detection pulse potentials would not observe this response.

The present method will now be further described by use of the following examples.

EXAMPLE 1

(Comparison of CE-ECD with CE-UV for Drug Detection)

Figure 7:
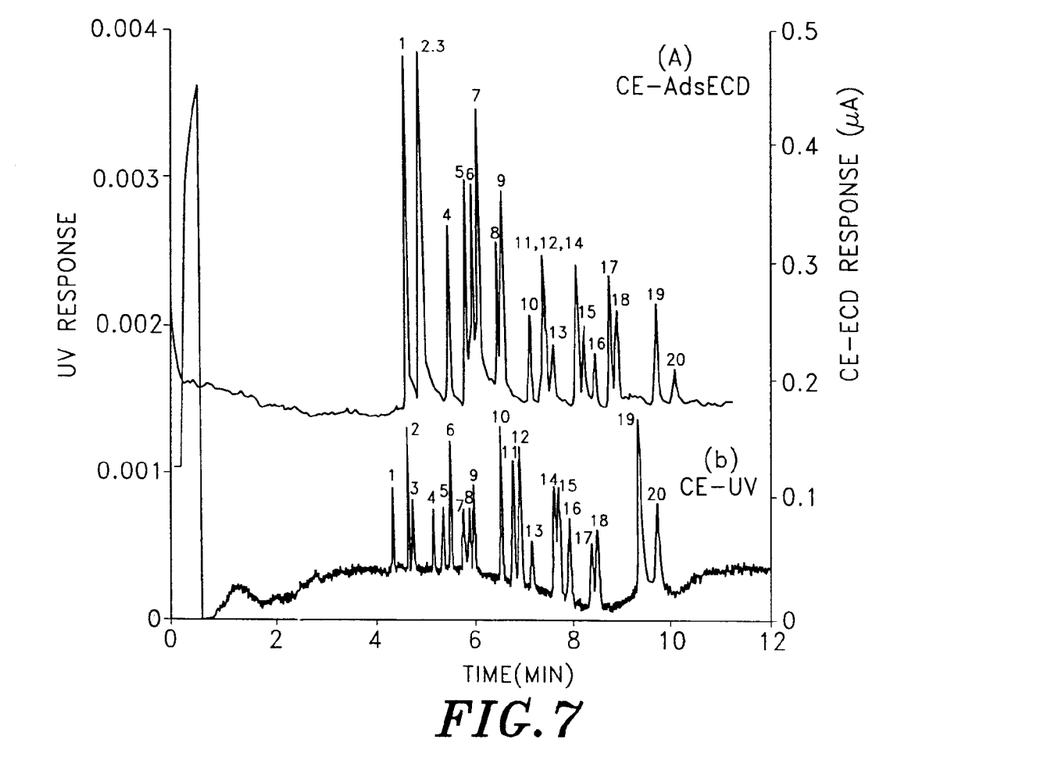
FIG. 7 is an electropherogram comparing results of the preferred embodiment with UV detection of several basic drugs commonly analyzed in forensic laboratories.

FIG. 7 illustrates the detection of numerous drugs and other residue of interest to forensic analysis using the ECD of the preferred embodiment (a) compared to analysis of the same drugs using a UV detection method (b). As noted in the Background section above, a common detection method used in conjunction with capillary electrophoresis (CE). The CE separation employed a 100 millimolar, pH 2.38 phosphate buffer. The samples were derived from a standard 1 ppm quality control drug mixture employed by the Royal Canadian Mounted Police (RCMP) for calibrating drug tests. In connection with the preferred ECD method (plot a), the mixture was injected electrokinetically for 1 s at 10 kV into the CE separation apparatus. In connection with the UV method (plot b), the mixture was pressure injected for 5 s at 0.5 p.s.i. (CE-UV, plot b).

The preferred ECD was conducted using a Pt working electrode with a diameter of 25 $\mu$m. The reference electrode used was an Ag|AgCl electrode. Square wave voltammetry was used during the analytical pulse, using similar parameters as those discussed with respect to FIGS. 4 and 5.

The results indicate equivalent or better sensitivities using ECD. Moreover, most of the tested drugs are not considered electrochemically active and would not respond to more traditional electrochemical detection methods (e.g., pulsed amperometric detection). Accordingly, the preferred embodiments represent a considerable advancement in enabling ECD for analytes previously undetectable with similar methods.

Although all of these drugs and analytes have widely varied chemical structure, they respond similarly to the preferred ECD methods. This is unusual for most traditional electrochemical detection methods where, typically, operation parameters (i.e., electrode detection potentials) must be adjusted to respond to different molecular structures.

EXAMPLE 2

(CE-ECD for Polypeptides)

Figure 8:
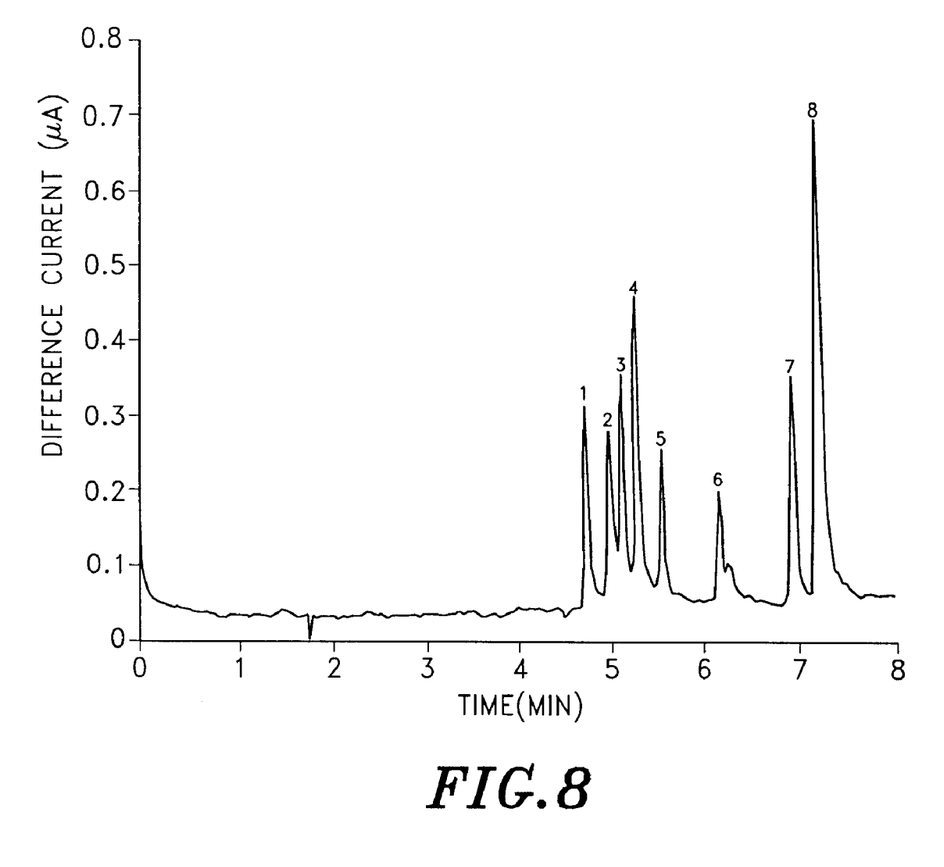
FIG. 8 is an electropherogram illustrating the detection of polypeptides by the preferred methods.

FIG. 8 is a separation of polypeptides using the CE-ECD of the preferred embodiment. Separation conditions include a 50 millimolar, pH 3.0 phosphate buffer with a 10 kV separation voltage. A 1 $\mu$g/mL solution of peptides was injected into the CE apparatus for 2 s at 10 kV. The detection apparatus was as described above for the CE-ECD analysis of drugs.

The strong signals generated by the preferred ECD methods illustrate the wide applicability of the illustrated ECD methods to biomolecules. Like many of the drugs listed on FIG. 7, the detected peptides are considered electrochemically inactive and thus would not respond to more traditional electrochemical detection methods.

Although described in the context of certain preferred embodiments, the skilled artisan will appreciate that various changes and modifications can be made to the preferred embodiments, and such changes and modifications are meant to be encompassed by the invention, as defined by the appended claims.

We claim:

1. A method for electrochemical detection of an analyte in a fluid, comprising;
   providing a working electrode with a diameter of about 1 $\mu$m to 100 $\mu$m in association with the fluid;
   applying a first positive potential pulse to the fluid at the working electrode, at a voltage of less than about 1,000 mV.
   applying a negative analytical potential pulse to the fluid at the working electrode at a voltage between about 0 mV and −2,000 mV; and
   measuring the current flow through the working electrode during the analytical potential pulse.

2. The method of claim 1, wherein the fluid flows across the working electrode during the analytical potential pulse.

3. The method of claim 1, further comprising applying a second positive potential pulse to the fluid at a voltage higher than the first positive potential pulse and between about 700 mV and 3,000 mV.

4. The method of claim 1, wherein each of the first positive potential pulse and the analytical potential pulse are conducted for between about 1 ms and 100 ms.

5. The method of claim 1, wherein the first positive potential pulse and the negative analytical potential pulse are conducted in a single cycle, and the single cycle is repeated at greater than 5 Hz.

6. The method of claim 1, further comprising applying a negative stabilizing potential pulse after the first positive potential-analytical pulse to the working electrode at a voltage of about 0 mV to −2,000, for about 1 to 100 ms.

7. The method of claim 1, wherein the analytical potential pulse comprises a scan across a range of negative potentials.

8. The method of claim 7, wherein the analytical potential pulse comprises a square waveform superimposed on a DC ramp.

9. The method of claim 7, wherein the analytical potential pulse comprises a scan across voltages within the range of between about −500 mV and −1,200 mV.

10. The method of claim 1, wherein the analytical potential pulse comprises a fixed potential at a voltage between about −200 to −2,000 mV.

11. The method of claim 1, wherein the working electrode has a diameter of less than about 100 $\mu$m.

12. The method of claim 11, wherein the working electrode has a diameter of less than about 50 $\mu$m.

13. The method of claim 1, wherein the working electrode comprises a metal.

14. The method of claim 13, wherein the working electrode is selected from the group consisting of platinum (Pt), palladium (Pd), gold (Au), ruthenium (Ru), rhodium (Rh), osmium (Os) and iridium (Ir).

15. The method of claim 1, wherein the analyte comprises an organic species.

16. The method of claim 15, wherein the analyte comprises a polypeptide.

17. The method of claim 15, wherein the analyte comprises a therapeutic agent or diagnostic substance employed in human or veterinary medicines.

18. The method of claim 15, wherein the analyte comprises a pesticide.

19. The method of claim 1, wherein the first positive potential pulse comprises a voltage less than about 800 mV.

20. The method of claim 19, wherein the first positive potential pulse comprises a voltage between about 300 mV and 600 mV.

21. The method of claim 20, wherein the first positive pulse is at a voltage of about 400 mV.

22. The method of claim 20, further comprising applying a second positive potential pulse to the fluid at a voltage higher than the first positive potential pulse and between about 800 mV to 2,000 mV.

23. The method of claim 1, wherein the fluid flows from a capillary electrophoresis separation system.

24. The method of claim 1, wherein applying the first positive potential pulse to the fluid comprises powering an auxiliary electrode immersed in a buffer solution, and wherein the fluid flows into the buffer solution.

25. A method for electrochemical detection of organic analytes, wherein one detection cycle comprises:

separating a sample of organic analytes using capillary electrophoresis;

providing the separated analytes in a flowing stream to a surface of a working electrode;

applying at least one positive potential pulse to the analytes at the working electrode for between about 1 ms and 100 ms; and applying a negative analytical pulse to the working electrode at voltages between about −300 mV and −1,500 mV versus an Ag|AgCl electrode, for between about 1 ms to 100 ms; and measuring current through the working electrode during the negative analytical pulse.

26. The method of claim 25, wherein the at least one positive potential comprises a pre-analytical preparatory pulse at between about 300 mV and 600 mV and a post-analytical cleaning pulse at between about 700 mV and 3,000 mV, each for between about 1 ms and 100 ms.

27. The method of claim 25, wherein the negative analytical pulse comprises a voltage scan from −600 mV to −1,100 mV.

28. The method of claim 25, further comprising applying a negative stabilizing potential pulse after the first positive potential-analytical pulse to the working electrode at a voltage of about 0 mV to −2,000 mV versus an Ag|AgCl electrode, for about 1 to 100 ms.

29. The method of claim 25, wherein the sample has a concentration of analytes of less than about $10^{-5}$ molar.

30. The method of claim 29, wherein the sample has a concentration of analytes of less than about $10^{-7}$ molar.

31. An electrochemical detector, comprising electronic hardware and software controlling voltage applied to a sample fluid, the hardware and software configured to apply a voltage in repeated cycles of pulses where each cycle includes:

a positive electrode preparation pulse of a first magnitude;

a negative analytical pulse; and a positive cleaning pulse of a second magnitude greater than the first magnitude.

32. The electrochemical detector of claim 31, configured such that each cycle further comprises a negative stabilizing pulse between the electrode preparation pulse and the analytical pulse.

* * * * *